US00PP35788P3

(12) United States Plant Patent
Glawe et al.

(10) Patent No.: US PP35,788 P3
(45) Date of Patent: Apr. 30, 2024

(54) ***PELARGONIUM* PLANT NAMED 'KLEIP22654'**

(50) Latin Name: *Pelargonium interpeltatum*
Varietal Denomination: KLEIP22654

(71) Applicant: KLEMM + SOHN GMBH & CO. KG, Stuttgart (DE)

(72) Inventors: Martin Glawe, Stuttgart (DE); Nina Neu, Weissach im Tal (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/312,439

(22) Filed: May 4, 2023

(65) Prior Publication Data

US 2023/0371413 P1 Nov. 16, 2023

(30) Foreign Application Priority Data

May 16, 2022 (CH) ..... 22-3520

(51) Int. Cl.
*A01H 5/02* (2018.01)
*A01H 6/42* (2018.01)

(52) U.S. Cl.
USPC ..... Plt./324
CPC ..... *A01H 6/425* (2018.05)

(58) Field of Classification Search
USPC ..... Plt./324, 330, 332
CPC ..... A01H 5/02
See application file for complete search history.

*Primary Examiner* — Kent L Bell
(74) *Attorney, Agent, or Firm* — Weatherly IP Solutions, LLC; James M. Weatherly

(57) ABSTRACT

A new *Pelargonium* plant particularly distinguished by a dark red flower color, single flower filling, a lack of zonation, leaf margins with a deep sinus of crenate margin, and light green leaves, is disclosed.

1 Drawing Sheet

Genus and species: *Pelargonium interpeltatum.*
Variety denomination: 'KLEIP22654'.

CROSS-REFERENCE TO RELATED APPLICATION

This patent application claims the benefit of priority from Switzerland Plant Breeders Rights Application No. 22-3520 as filed on May 16, 2022, the contents of which is incorporated herein by reference for all it teaches and discloses.

BACKGROUND OF THE NEW PLANT

The present invention comprises a new and distinct variety of *Pelargonium*, botanically known as *Pelargonium interpeltatum* and hereinafter referred to by the variety name 'KLEIP22654'. 'KLEIP22654' originated from a controlled cross in August 2017 in Nairobi, Kenya between the proprietary female *Pelargonium* variety 'KLEIP13348' (unpatented) and the proprietary male *Pelargonium* variety 'PIP-2016-6447' (unpatented).

Seeds from the controlled-cross were obtained. The seeds were sown and plants were grown for evaluation. A single plant was selected in June 2018 and subsequently named 'KLEIP22654'. In July 2018 'KLEIP22654' was first vegetatively propagated by vegetative stem cuttings in Stuttgart, Germany. 'KLEIP22654' was found to reproduce true to type in successive generations of asexual propagation via stem cuttings in Stuttgart, Germany.

SUMMARY

The following are the most outstanding and distinguishing characteristics of this new variety when grown under normal horticultural practices in Latina, Italy.

1. Dark red flower color;
2. Single flower filling;
3. No Zonation;
4. Leaf margins with a deep sinus of crenate margin; and
5. Light green leaves.

DESCRIPTION OF THE PHOTOGRAPH

This new *Pelargonium* plant is illustrated by the accompanying photograph which shows an overall view of the plant in a pot. The photograph is of an approximately 14-week-old plant grown outdoors in Stuttgart, Germany, in July 2021. The colors shown are as true as can be reasonably obtained by conventional photographic procedures.

DESCRIPTION OF THE NEW VARIETY

The following detailed descriptions set forth the distinctive characteristics of 'KLEIP22654'. Data was collected on 19-week-old plants in Latina, Italy under greenhouse conditions in April 2023. Color references are to The R.H.S. Colour Chart of The Royal Horticultural Society of London (R.H.S.), 5$^{th}$ edition (2007).

Classification:
*Family.*—Geraniaceae.
*Botanical.*—*Pelargonium interpeltatum.*
*Common.*—*Pelargonium.*
*Designation.*—'KLEIP22654'.

Parentage:
*Female parent.*—'KLEIP13348' (unpatented).
*Male parent.*—'PIP-2016-6447' (unpatented).

Plant:
*Form.*—Bushy.
*Habit.*—Mounding.
*Height* (*from top of soil*).—23.0 cm.
*Width* (*horizontal plant diameter*).—31.0 cm.
*Natural flowering season.*—March to October.
*Propagation type.*—Vegetative by stem cuttings.
*Time to produce a finished flowering plant.*—12 weeks.
*Time to initiate and develop roots.*—4 weeks.
*Root description.*—Fine, dense, white (RHS N155B).
Stems:
*Quantity of stems per plant.*—8 to 10 .
*Color.*—RHS 146B.
*Surface texture.*—Pubescent.
*Stem form.*—Round.
*Diameter.*—0.5 cm.
*Length.*—9.0 cm.
*Internode length.*—3.4 cm.
*Anthocyanin.*—Absent.
Leaves:
*Arrangement.*—Alternate.
*Shape.*—Reniform.
*Apex.*—Round.
*Base.*—Open.
*Margin.*—Crenate.
*Surface texture both surfaces.*—Pubescent.
*Length.*—9.5 cm.
*Width.*—10.0 cm.
*Color.*—Upper surface: RHS 137 B. Lower surface: RHS 146 B.
*Zonation.*—None.
*Depth of sinus.*—2.0 cm.
*Petiole.*—Length: 6.0 cm. Diameter: 0.3 cm. Color: RHS 146B. Strength: Medium.
*Venation pattern.*—Palmate.
*Venation color.*—Upper surface: RHS 137B. Lower surface: RHS 146B.
Inflorescence:
*Lastingness of flowers on the plant.*—6 to 8 days.
*Umbels.*—Quantity of umbels per plant: 8 to 10. Length: 6.7 cm. Diameter: 8.5 cm.
*Individual florets of the umbel.*—Quantity of florets per umbel: 22 to 28. Depth: 2.3 cm. Diameter: 5.7 cm.
*Fragrance.*—Absent.
Flower buds:
*Cluster shape.*—Round.
*Cluster size.*—Length: 2.6 cm. Width: 2.5 cm.
*Surface texture.*—Pubescent.
*Bud.*—Height: 1.5 cm. Width: 0.5 cm. Shape: Elliptic. Apex: Acute. Base: Obtuse. Margin: Entire. Color: RHS 146B.
Petals:
*Quantity per flower.*—5.
*Shape*—Spatulate.
*Apex.*—Round.
*Base.*—Obtuse.
*Margin.*—Entire.
*Length.*—3.2 cm.
*Width.*—2.2 cm.
*Surface texture.*—Upper surface: Smooth. Lower surface: Smooth.
*Color of lobes.*—Upper lobes: Upper surface: RHS 46A. Lower surface: RHS 53C. Lower lobes: Upper surface: RHS 46A. Lower surface: RHS 53C.
Petaloids: Absent.
Sepals:
*Number per flower.*—5.
*Shape.*—Elliptic.
*Apex.*—Acute.
*Base.*—Obtuse.
*Margin.*—Entire.
*Surface texture.*—Upper surface: Smooth. Lower surface: Pubescent.
*Color.*—Upper surface: RHS 146B. Lower surface: RHS 146B.
*Length.*—1.6 cm.
*Width.*—0.5 cm.
Pedicel:
*Length.*—2.4 cm.
*Diameter.*—0.2 cm.
*Color.*—RHS 144A with a touch of RHS 174B.
*Surface texture.*—Pubescent.
*Strength.*—Weak.
Peduncle:
*Length.*—17.5 cm.
*Diameter.*—0.3 cm.
*Color.*—RHS 144A with sometimes RHS 174A on one side.
*Texture.*—Pubescent.
*Strength.*—Medium.
Reproductive organs:
*Stamens.*—Quantity per flower: 5 to 7. Anther length: 0.2 cm. Filament length: 0.9 cm. Filament color: RHS N155A with RHS 51B at the tips. Pollen amount: Medium. Pollen color: RHS N172A.
*Pistils.*—Number: 1. Stigma color: RHS 46A. Style length: 0.2 cm. Style color: RHS 51C. Ovary arrangement: Central. Ovary color: RHS 144B. Ovary diameter: 0.2 cm. Ovary length: 0.5 cm. Ovary Texture: Pubescent.
Fruit and seed set: None observed.
Disease and pest/insect resistance: None observed.

COMPARISON WITH PARENTAL LINES AND KNOWN VARIETY

'KLEIP22654' is distinguished from its parents as described in Table 1.

TABLE 1

Comparison with Parental Lines

| Characteristic | 'KLEIP22654' | Female parent | Male parent |
|---|---|---|---|
| Flower Color | Dark red | Magenta | Dark red |
| Flower Filling | Single | Single | Semidouble |

'KLEIP22654' can be compared to the commercial variety 'Two-in-One Dark Red' (patent status unknown). Differences between the two varieties are described in Table 2:

TABLE 2

Comparison with Similar Variety

| Characteristic | 'KLEIP22654' | 'Two-in-One Dark Red' |
|---|---|---|
| Zonation | None | Very weak |
| Leaf margins | Deep sinus of crenate margin | Weak sinus of crenate margin |
| Leaf Color | Light green | Medium green |

We claim:

1. A new and distinct variety of *Pelargonium* plant named 'KLEIP22654' as illustrated and described herein.

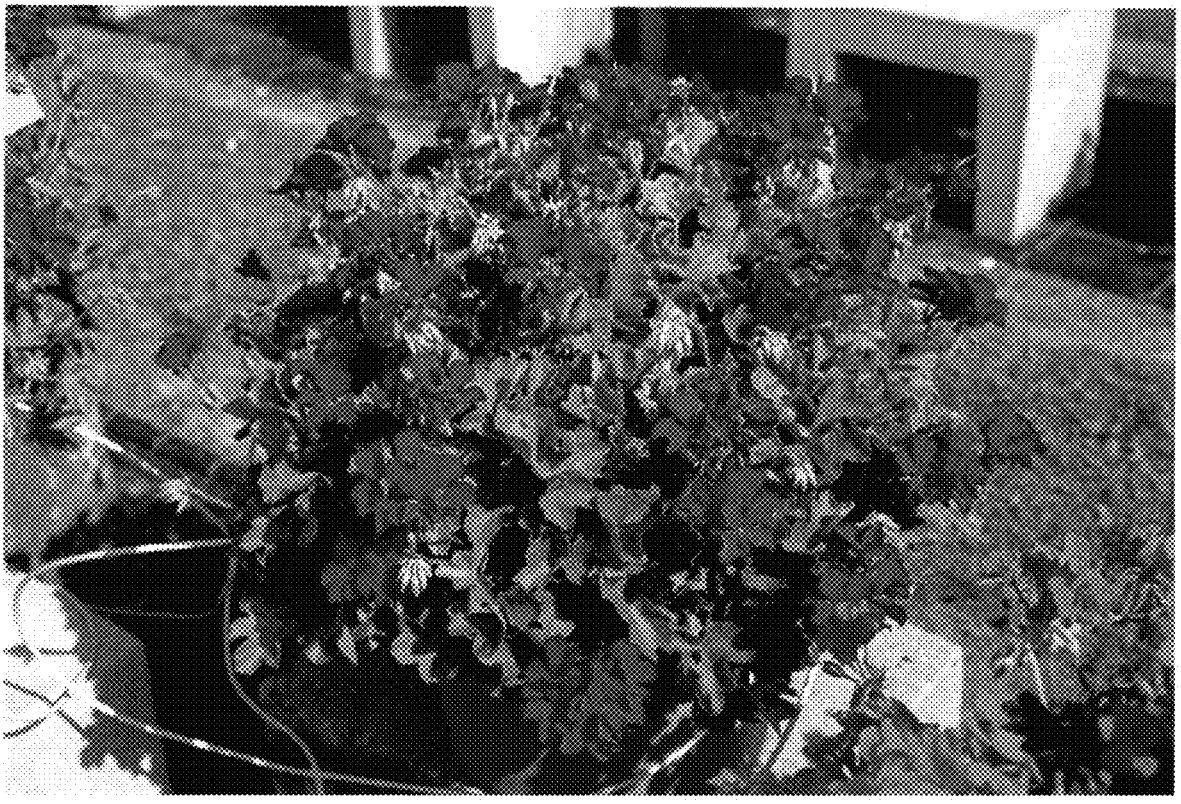

* * * * *